(12) United States Patent
Tsurumi

(10) Patent No.: US 10,546,194 B2
(45) Date of Patent: Jan. 28, 2020

(54) INFORMATION PROCESSING APPARATUS, INFORMATION PROCESSING METHOD, AND PROGRAM

(71) Applicant: SONY CORPORATION, Tokyo (JP)

(72) Inventor: Shingo Tsurumi, Saitama (JP)

(73) Assignee: SONY CORPORATION, Tokyo (JP)

( * ) Notice: Subject to any disclaimer, the term of this patent is extended or adjusted under 35 U.S.C. 154(b) by 258 days.

(21) Appl. No.: 15/511,489

(22) PCT Filed: Sep. 3, 2015

(86) PCT No.: PCT/JP2015/075140
§ 371 (c)(1),
(2) Date: Mar. 15, 2017

(87) PCT Pub. No.: WO2016/088418
PCT Pub. Date: Jun. 9, 2016

(65) Prior Publication Data
US 2017/0293794 A1    Oct. 12, 2017

(30) Foreign Application Priority Data
Dec. 2, 2014  (JP) ................. 2014-243907

(51) Int. Cl.
*G06K 9/00* (2006.01)
*G06T 7/70* (2017.01)

(52) U.S. Cl.
CPC ....... *G06K 9/0061* (2013.01); *G06K 9/00604* (2013.01); *G06T 7/70* (2017.01); *G06T 2207/30201* (2013.01)

(58) Field of Classification Search
None
See application file for complete search history.

(56) References Cited

U.S. PATENT DOCUMENTS

| | | | | |
|---|---|---|---|---|
| 5,627,621 A | * | 5/1997 | Kodama | G03B 13/02 351/208 |
| 2007/0014552 A1 | * | 1/2007 | Ebisawa | A61B 3/113 396/51 |
| 2014/0300867 A1 | * | 10/2014 | Fassi | A61N 5/1017 351/209 |
| 2015/0374223 A1 | * | 12/2015 | Shudo | A61B 3/113 351/210 |
| 2016/0077585 A1 | * | 3/2016 | Mizuhara | G06F 3/013 345/157 |

* cited by examiner

Primary Examiner — Frederick D Bailey
(74) Attorney, Agent, or Firm — Paratus Law Group, PLLC

(57) ABSTRACT

Provided is an information processing apparatus including: a detection unit configured to detect a corneal reflection image corresponding to light from a light source reflected at a cornea from a captured image in which an eye irradiated with the light from the light source is imaged. The detection unit estimates a position of a center of an eyeball on the basis of a plurality of time-series captured images each of which is the captured image according to the above, estimates a position of a center of the cornea on the basis of the estimated position of the center of the eyeball, estimates a position of a candidate for the corneal reflection image on the basis of the estimated position of the center of the cornea, and detects the corneal reflection image from the captured image on the basis of the estimated position of the candidate for the corneal reflection image.

12 Claims, 11 Drawing Sheets

INFORMATION PROCESSING APPARATUS, INFORMATION PROCESSING METHOD, AND PROGRAM

CROSS REFERENCE TO PRIOR APPLICATION

This application is a National Stage Patent Application of PCT International Patent Application No. PCT/JP2015/075140 (filed on Sep. 3, 2015) under 35 U.S.C. § 371, which claims priority to Japanese Patent Application No. 2014-243907 (filed on Dec. 2, 2014), which are all hereby incorporated by reference in their entirety.

TECHNICAL FIELD

The present disclosure relates to an information processing apparatus, an information processing method, and a program.

BACKGROUND ART

As an example of the method used for the estimation of an eye gaze, there is a method using the corneal reflection method that uses a corneal reflection image (also called a "Purkinje image") formed by the reflection of the light of a light source at the cornea. Examples of the technology that measures an eye gaze using the corneal reflection method include the technology described in Non-Patent Literature 1 below.

CITATION LIST

Non-Patent Literature

Non-Patent Literature 1: Takehiko Ohno, Naoki Mukawa, and Atsushi Yoshikawa, "*Gankyu keyjo moderu ni motozuku shisen sokutei-ho* (Eye gaze measurement method based on eyeball shape model)," The 8th Symposium on Sensing Via Image Information, pp. 307-312

DISCLOSURE OF INVENTION

Technical Problem

In the case of using the corneal reflection method, for example, an eye irradiated with the light from light sources, such as near-infrared light generated by point light sources, is imaged by an imaging device, and the positions of a plurality of corneal reflection images included in the captured image of the eye irradiated with the light from the light sources (hereinafter, occasionally referred to as simply a "captured image") are identified; thereby, the position of the center of the cornea (the three-dimensional position of the center of the cornea (the center of curvature of the cornea)) can be found. When the position of the center of the cornea is found, a vector corresponding to the eye gaze can be found.

However, an outlier that appears like a corneal reflection image, such as an unexpected appearance of the light of another light source than the light sources mentioned above for obtaining corneal reflection images (for example, illumination etc.) and a reflection at the edge of a contact lens worn on the eye, may be included in the captured image. If the position of an outlier is falsely identified as being the position of a corneal reflection image, the finding of a vector corresponding to the eye gaze with good accuracy is not expected, for example.

The present disclosure proposes a new and improved information processing apparatus, a new and improved information processing method, and a new and improved program by which a corneal reflection image can be detected from a captured image.

Solution to Problem

According to the present disclosure, there is provided an information processing apparatus including: a detection unit configured to detect a corneal reflection image corresponding to light from a light source reflected at a cornea from a captured image in which an eye irradiated with the light from the light source is imaged. The detection unit estimates a position of a center of an eyeball on the basis of a plurality of time-series captured images each of which is the captured image according to the above, estimates a position of a center of the cornea on the basis of the estimated position of the center of the eyeball, estimates a position of a candidate for the corneal reflection image on the basis of the estimated position of the center of the cornea, and detects the corneal reflection image from the captured image on the basis of the estimated position of the candidate for the corneal reflection image.

According to the present disclosure, there is provided an information processing method executed by an information processing apparatus, the method including: a step of detecting a corneal reflection image corresponding to light from a light source reflected at a cornea from a captured image in which an eye irradiated with the light from the light source is imaged, the step of detection including estimating a position of a center of an eyeball on the basis of a plurality of time-series captured images each of which is the captured image according to the above, estimating a position of a center of the cornea on the basis of the estimated position of the center of the eyeball, estimating a position of a candidate for the corneal reflection image on the basis of the estimated position of the center of the cornea, and detecting the corneal reflection image from the captured image on the basis of the estimated position of the candidate for the corneal reflection image.

According to the present disclosure, there is provided a program for causing a computer to execute: a step of detecting a corneal reflection image corresponding to light from a light source reflected at a cornea from a captured image in which an eye irradiated with the light from the light source is imaged, the step of detection including estimating a position of a center of an eyeball on the basis of a plurality of time-series captured images each of which is the captured image according to the above, estimating a position of a center of the cornea on the basis of the estimated position of the center of the eyeball, estimating a position of a candidate for the corneal reflection image on the basis of the estimated position of the center of the cornea, and detecting the corneal reflection image from the captured image on the basis of the estimated position of the candidate for the corneal reflection image.

Advantageous Effects of Invention

According to the present disclosure, a corneal reflection image can be detected from a captured image.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
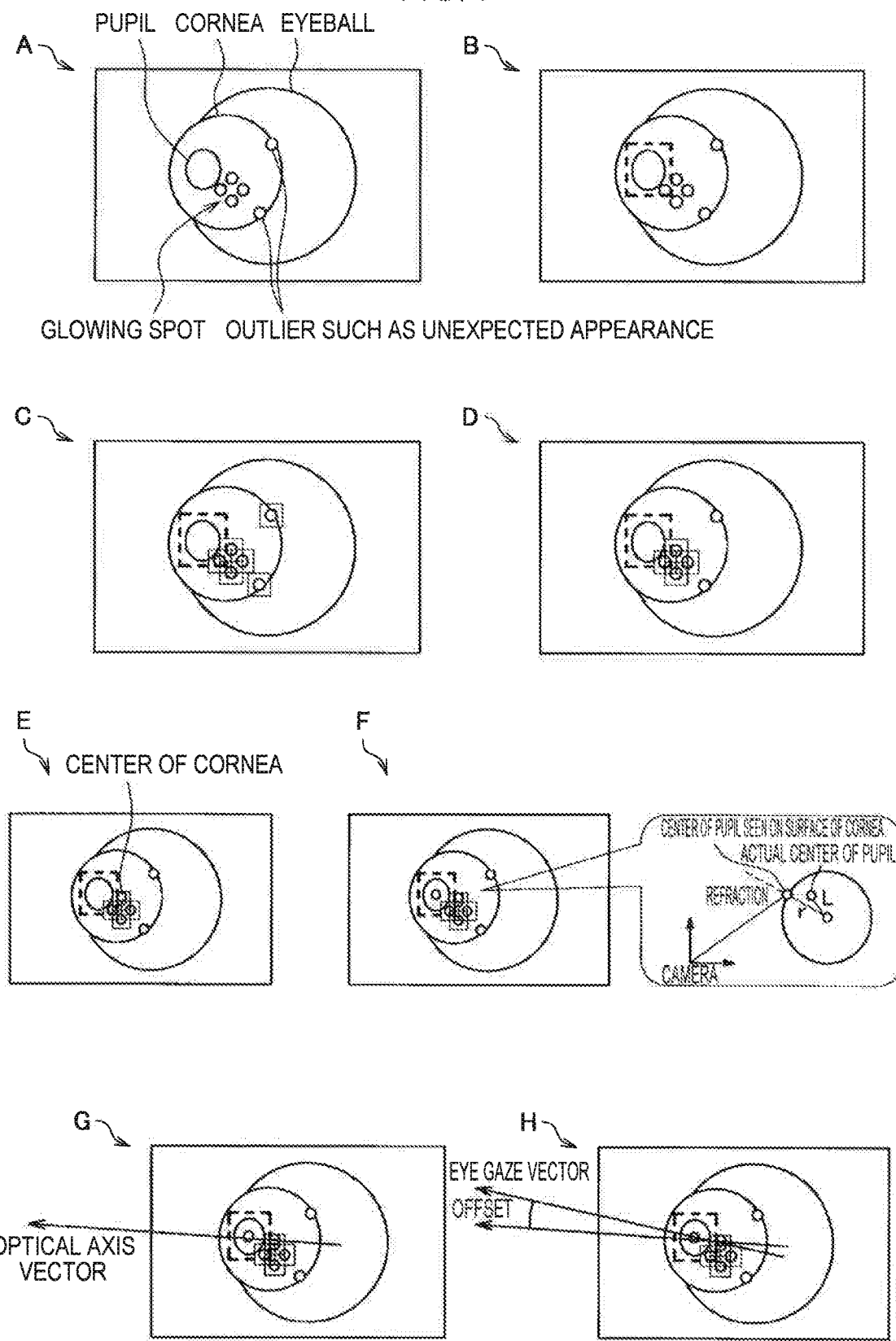
FIG. 1 is an explanatory diagram for describing a method for detecting a corneal reflection image from a captured image.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

In the following, the description is given in the following order.
1. Information processing method according to the present embodiment
2. Information processing apparatus according to the present embodiment
3. Program according to the present embodiment
(Information Processing Method According to the Present Embodiment)

Before describing the configuration of an information processing apparatus according to the present embodiment, first an information processing method according to the present embodiment is described. In the following, the information processing method according to the present embodiment is described using, as an example, the case where an information processing apparatus according to the present embodiment performs processing according to the information processing method according to the present embodiment.

As described above, in a captured image of an eye irradiated with the light from a light source, not only a corneal reflection image but also an outlier that appears like a corneal reflection image may be included.

Here, examples of the light source according to the present embodiment include an infrared light emitting diode (IR LED). The light source according to the present embodiment is not limited to a light source that emits infrared light such as an IR LED, and may be a light source that emits light of any wavelength at which a corneal reflection image can be detected from a captured image. In the following, the corneal reflection image corresponding to the light source according to the present embodiment may be referred to as a "glowing spot."

Examples of the captured image according to the present embodiment include a captured image captured by an imaging device included in a device usable by being worn on the user's head. The captured image according to the present embodiment may be a captured image captured by an external imaging device connected to the device usable by being worn on the user's head mentioned above.

Examples of the device usable by being worn on the user's head according to the present embodiment include an eyewear (for example, an eyeglass type (including one-eyeglass type) device), a head-mounted display (HMD), and the like. The light source according to the present embodiment may be, for example, a light source included in a device usable by being worn on the user's head according to the present embodiment, or may be an external light source connected to a device usable by being worn on the user's head according to the present embodiment.

The captured image according to the present embodiment is not limited to an image captured by an imaging device included in a device usable by being worn on the user's head or an external imaging device connected to a device usable by being worn on the user's head. For example, the captured image according to the present embodiment may be an image captured by any imaging device capable of imaging an eye irradiated with the light from a light source. Further, the light source according to the present embodiment may be a light source included in a certain device, or may be an independent light source independent of other devices. The light source according to the present embodiment is provided in a position that allows the generated light to be applied to the user's eye, for example.

In the following, the case where the captured image according to the present embodiment is an image captured by an imaging device included in a device usable by being worn on the user's head (or an external imaging device connected to a device usable by being worn on the user's head) is mainly used as an example. In the following, the imaging device may be referred to as a "camera."

[1] Example of Method for Detecting Corneal Reflection Image

Here, as a method for detecting a corneal reflection image from a captured image, a method in which a candidate for the corneal reflection image existing in a position where the probability of existence of a corneal reflection image is presumed to be high in view of a score of a corneal reflection image detector constructed using machine learning or the like, the position of appearance of the pupil, or the like is detected as a correct corneal reflection image may be possible, for example.

However, as described later, in the one method mentioned above for detecting a corneal reflection image from a captured image, it is not always possible for a corneal reflection image to be correctly detected from a captured image.

FIG. 1 is an explanatory diagram for describing a method for detecting a corneal reflection image from a captured image. FIG. 1 shows, for convenience of description, an example of a series of processing that uses a method for detecting a corneal reflection image from a captured image to estimate a vector corresponding to an eye gaze (an optical axis vector and an eye gaze vector described later; hereinafter, occasionally referred to as an "eye axis vector").

Here, A of FIG. 1 shows an example of the captured image. As shown in A of FIG. 1, a pupil, glowing spots on a cornea (corneal reflection images), outliers of the glowing spot, etc. are included in the captured image, for example. A of FIG. 1 shows an example in which four glowing spots corresponding to the light from four light sources are included in the captured image.

B of FIG. 1 to H of FIG. 1 show an example of a series of processing of the estimation of a vector corresponding to an eye gaze that is performed on the captured image shown in A of FIG. 1.

Hereinbelow, while a series of processing that estimates a vector corresponding to the eye gaze shown in FIG. 1 is described, the reason why using the one method for detecting a corneal reflection image from a captured image does not always allow a corneal reflection image to be correctly detected from a captured image is described. In the following, the case where an information processing apparatus performs the processing shown in FIG. 1 is used as an example.

The processing that estimates a vector corresponding to the eye gaze consists of the seven steps described in (i) to (vii) below, for example.

(i) First Step: Detection of Pupil by Image Recognition (B of FIG. 1)

The information processing apparatus detects the pupil from the captured image shown in A of FIG. 1.

The information processing apparatus detects the pupil by converting the captured image to two values and assessing an area including the pupil, for example. The method for detecting the pupil from the captured image is not limited to the example described above. For example, the information processing apparatus may use any method that can detect the pupil from an image, such as "a method using the feature value of pixel difference (for example, the difference between the pixel values (luminance values) of each of a plurality of combinations of two pixels set on an image; this similarly applies hereinafter) and boosting technology."

(ii) Second Step: Detection of Candidate for Corneal Reflection Image by Image Recognition (C of FIG. 1)

The information processing apparatus detects a candidate for the corneal reflection image using "a method using the feature value of pixel difference and boosting technology," for example.

Here, as described above, an outlier that appears like a corneal reflection image may exist in the captured image. Hence, in the case where a candidate for the corneal reflection image is detected by image recognition using a method like the above, the corneal reflection image and the outlier may be detected as a candidate for the corneal reflection image.

(iii) Third Step: Detection of Corneal Reflection Image (D of FIG. 1)

The information processing apparatus sets the range of existence of corneal reflection images on the basis of the position of the pupil identified from the captured image (hereinafter, referred to as "the position of appearance of the pupil"), and selects not more than four candidates for the corneal reflection image, which number is the same as the number of light sources, from the candidates for the corneal reflection image existing in the range of existence; thereby, detects corneal reflection images, for example. The information processing apparatus may detect corneal reflection images also by selecting not more than four candidates for the corneal reflection image, which number is the same as the number of light sources, on the basis of a score of a corneal reflection image detector constructed using machine learning or the like, for example.

Here, the processing mentioned above in the third step falls under processing according to the one method for detecting a corneal reflection image from a captured image.

However, in processing according to the one method for detecting a corneal reflection image from a captured image like the above, it is difficult to exclude outliers other than large outliers. Hence, in the case where processing according to the one method for detecting a corneal reflection image from a captured image like the above is performed, it is feared that a candidate for the corneal reflection image falling under an outlier will be detected as a corneal reflection image.

Hence, in the case of using the one method for detecting a corneal reflection image from a captured image, it is not always possible for a corneal reflection image to be correctly detected from a captured image.

Furthermore, the corneal reflection image is used in a step described later, therefore, when a candidate for the corneal reflection image falling under an outlier is detected as a corneal reflection image, the accuracy of estimation of a vector corresponding to the eye gaze is reduced.

Furthermore, in the case of using the one method for detecting a corneal reflection image from a captured image, when the number of candidates for the corneal reflection image selected is three or less, that is, the number of corneal reflection images detected is smaller than the number of light sources, it is difficult to associate the ID of the light source with the corneal reflection image or the like to make an association between the light source and the corneal reflection image. Here, when an error has occurred in the association between the light source and the corneal reflection image, a reduction in the accuracy of estimation of a vector corresponding to the eye gaze may be caused.

(iv) Fourth Step: Estimation of Position (Three-Dimensional Position) of Center of Cornea Using Positions of Corneal Reflection Images (E of FIG. 1)

The information processing apparatus estimates the position of the center of the cornea on the basis of information (data) concerning the eye such as the positions (u and v coordinates) of the plurality of detected corneal reflection images, the positions of the light sources, and the radius of the cornea (the curvature radius of the cornea), for example.

Here, the value shown by information concerning the eye according to the present embodiment such as the curvature radius of the cornea and other information described later (for example, data showing a value related to the eye such as the distance between the center of the eyeball and the center of the cornea and the distance between the center of the cornea and the center of the pupil) is a fixed value set in advance, for example. The value shown by information concerning the eye according to the present embodiment may be a value unique to the user, or may be a value standardized using the unique values of a plurality of users. In the case where the value shown by information concerning the eye according to the present embodiment is a value unique to the user, information concerning the eye corresponding to the user identified by any method that can authenticate the user, such as biometric authentication or password authentication, is used.

(v) Fifth Step: Estimation of Position (Three-Dimensional Position) of Center of Pupil (F of FIG. 1)

The information processing apparatus estimates the position of the center of the pupil using information concerning the eye such as the position of the center of the cornea estimated in the fourth step described in (iv) mentioned above, the distance L between the center of the cornea and the center of the pupil, and the radius r of the cornea, and the law of refraction, for example.

A processing similar to the processing of the fifth step is performed also in processing according to an information processing method according to the present embodiment described later. Hence, a description of an example of the processing of the fifth step is omitted.

(vi) Sixth Step: Estimation of Optical Axis Vector (G of FIG. 1)

The information processing apparatus estimates an optical axis vector (an example of the vector corresponding to the eye gaze) using the position of the center of the cornea estimated in the fourth step described in (iv) mentioned above and the position of the center of the pupil estimated in the fifth step described in (v) mentioned above, for example.

The information processing apparatus takes a vector directed toward the outside of the eyeball and connecting the position of the center of the cornea and the position of the center of the pupil as the optical axis vector, for example. The method for detecting the optical axis vector is not limited to the example described above. Other examples of the method for detecting the optical axis vector according to the present embodiment are described later.

(vii) Seventh Step: Estimation of Eye Gaze Vector (H of FIG. 1)

An eye gaze vector that is a vector indicating the eye gaze (an example of the vector corresponding to the eye gaze) is a vector connecting the fovea centralis and the center of the cornea of the eye. As shown in H of FIG. 1, a shift may occur between the eye gaze vector and the optical axis vector.

The information processing apparatus corrects the optical axis vector estimated in the sixth step described in (vi) mentioned above using an offset value obtained by calibration, and thereby estimates the eye gaze vector, for example. The offset value according to the present embodiment may be a fixed value set in advance, for example.

A vector corresponding to the eye gaze is estimated by the seven steps described in (i) mentioned above to (vii) mentioned above, for example.

Here, in the case where processing according to the one method for detecting a corneal reflection image from a captured image is performed in the third step described in (iii) mentioned above, it is not always possible for a corneal reflection image to be correctly detected from a captured image, as described above.

Furthermore, the corneal reflection image estimated in the third step described in (iii) mentioned above influences the results of the pieces of processing described in (iv) mentioned above to (vii) mentioned above. Hence, in the case where processing according to the one method for detecting a corneal reflection image from a captured image is performed in the third step described in (iii) mentioned above, the accuracy of estimation of a vector corresponding to the eye gaze is reduced.

[2] Information Processing Method According to the Present Embodiment

In view of the above, an information processing apparatus according to the present embodiment detects a corneal reflection image from a captured image by performing the processing described in (1) to (4) below (detection processing), for example.

(1) Estimation of Position of Center of Eyeball

The information processing apparatus according to the present embodiment estimates the position of the center of the eyeball on the basis of a plurality of time-series captured images.

Examples of the plurality of time-series captured images according to the present embodiment include frame images (still images) constituting moving images. In the following, the frame image may be referred to as simply a "frame."

In the case where the corneal reflection method is used, the three-dimensional positions of the center of curvature of the cornea and the center of the pupil are found from a corneal reflection image and the position of the pupil observed on an image; but in the corneal reflection method, the three-dimensional position of the center of the eyeball cannot be directly estimated.

Thus, the information processing apparatus according to the present embodiment uses time-series captured images, and estimates, as the position of the center of the eyeball, the point of intersection of the optical axis vectors at the time points obtained on the basis of the plurality of captured images.

The optical axis vector at each time point is estimated by the processing described with reference to FIG. 1, for example. Here, in the case where processing using time-series captured images cannot be performed in the third step described in (iii) mentioned above, the one method for detecting a corneal reflection image from a captured image mentioned above is used; and in the case where processing using time-series captured images can be performed, the information processing method according to the present embodiment is used as well; thereby, the optical axis vector is estimated, for example. Further, by excluding outliers of the estimated optical axis vector, the reduction in the accuracy of estimation of the position of the center of the eyeball due to the influence of outliers can be prevented, for example.

Figure 2:
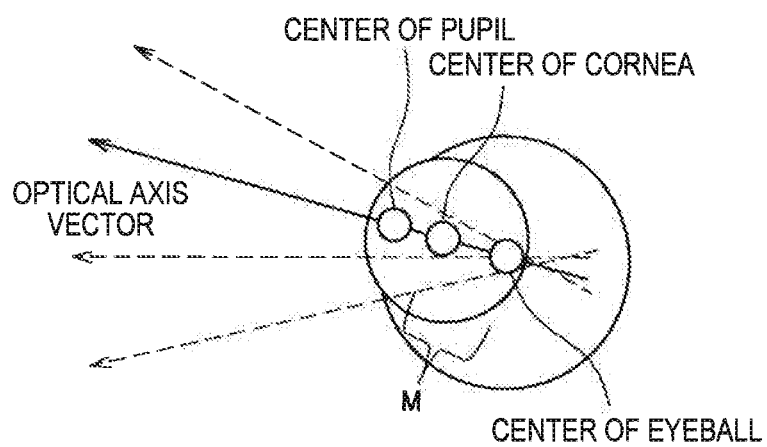
FIG. 2 is an explanatory diagram for describing an example of processing according to an information processing method according to the present embodiment.

FIG. 2 is an explanatory diagram for describing an example of the processing according to the information processing method according to the present embodiment, and shows an overview of processing for the estimation of the position of the center of the eyeball.

As shown in FIG. 2, optical axis vectors do not precisely cross at one point due to the influence of an error etc. Thus, the information processing apparatus according to the present embodiment takes the nearest point of a plurality of optical axis vectors as the position of the center of the eyeball.

Here, in the case where the device usable by being worn on the user's head according to the present embodiment is an eyewear such as an eyeglass-type wearable device and an imaging device is fixed to the device usable by being worn on the user's head, it can be assumed that, "unless a wearing slippage of the device usable by being worn on the user's head (an example of the change in the wearing state of the device usable by being worn on the user's head) occurs, the position of the center of the eyeball is fixed with respect to the imaging device."

Figure 3:
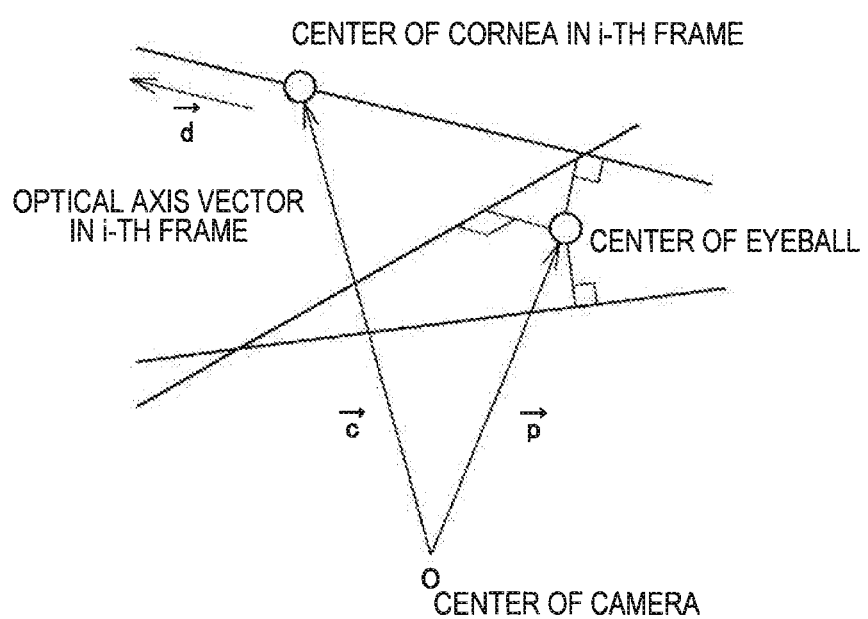
FIG. 3 is an explanatory diagram for describing an example of the processing according to the information processing method according to the present embodiment.

FIG. 3 is an explanatory diagram for describing an example of the processing according to the information processing method according to the present embodiment, and shows an overview of processing for the estimation of the position of the center of the eyeball. In FIG. 3, the position of the imaging device is shown as "the center of the camera," and an example in which the center of the camera is taken as the origin is shown. In the following, a vector may be written as "x$^\rightarrow$" for the sake of convenience.

As shown in FIG. 3, the position of the center of the cornea is denoted by "c$^\rightarrow$", the optical axis vector by "d$^\rightarrow$", and the position of the center of the eyeball desired to be found by "p$^\rightarrow$". Point $L_i$ on the i-th (i being a positive integer) optical axis vector is expressed by Mathematical Formula 1 below, for example. Here, "$t_i$" shown in Mathematical Formula 1 is an auxiliary variable.

[Math. 1]

$$\vec{L}_i = \vec{d}_i \cdot t_i + \vec{c}_i \qquad \text{Mathematical Formula 1}$$

The distance between the position of the center of the eyeball and point $L_i$ on the optical axis vector is expressed by Mathematical Formula 2 below.

[Math. 2]

$$|\vec{L}_i - \vec{p}_i| = |\vec{d}_i \cdot t_i + \vec{c}_i - \vec{p}_i| \qquad \text{Mathematical Formula 2}$$

Thus, the information processing apparatus according to the present embodiment finds a point that minimizes the sum of squares of the distances to point $L_i$ for all "i"s, and takes the found point as the position of the center of the eyeball, for example. Specifically, the information processing apparatus according to the present embodiment solves the n+1 (n being a positive integer) simultaneous equations shown in Mathematical Formula 3 below to find the value of p, and thereby estimates the position of the center of the eyeball, for example. Here, "F" shown in Mathematical Formula 3 below is expressed by Mathematical Formula 4 below, for example.

Mathematical Formula 3

$$\begin{cases} \frac{\partial F}{\partial t_i} = \frac{\partial}{\partial t_i} \begin{bmatrix} \frac{1}{2}\sum_{i=0}^{n-1}\{t_i^2 \cdot (\vec{d}_i^T \cdot \vec{d}_i)\} + \\ \frac{1}{2}\sum_{i=0}^{n-1}\{t_i \cdot \vec{d}_i^T \cdot (\vec{c}_i - \vec{p})\} + \\ \frac{1}{2}\sum_{i=0}^{n-1}\{(\vec{c}_i - \vec{p})^T \cdot (\vec{c}_i - \vec{p})\} \end{bmatrix} = \\ t_i \cdot (\vec{d}_i^T \cdot \vec{d}_i) + \vec{d}_i^T \cdot (\vec{c}_i - \vec{p}) = 0 \\ \frac{\partial F}{\partial \vec{p}} = -\sum_{i=0}^{n-1}(t_i \cdot \vec{d}_i + \vec{c}_i) + n\vec{p} = 0 \end{cases}$$ [Math. 3]

Mathematical Formula 4

$$F(t_0, t_1, \ldots t_{n-1}, \vec{p}) = \frac{1}{2}\sum_{i=0}^{n-1}|\vec{d}_i \cdot t_i + \vec{c}_i - \vec{p}_i|^2 \qquad \text{[Math. 4]}$$

(2) Estimation of Position of Center of Cornea

The information processing apparatus according to the present embodiment estimates the position of the center of the cornea on the basis of the position of the center of the eyeball estimated by the processing of (1) mentioned above.

Specifically, the information processing apparatus according to the present embodiment performs the processing of (2-1) and (2-2) below, and thereby estimates the position of the center of the cornea, for example.

(2-1) Estimation of Position of Center of Pupil

The information processing apparatus according to the present embodiment estimates the position of the center of the pupil on the basis of the position of the center of the eyeball estimated by the processing of (1) mentioned above. Here, the principle of the processing of (2-1) is similar to the processing of the fifth step shown in (v) mentioned above.

Figure 4:
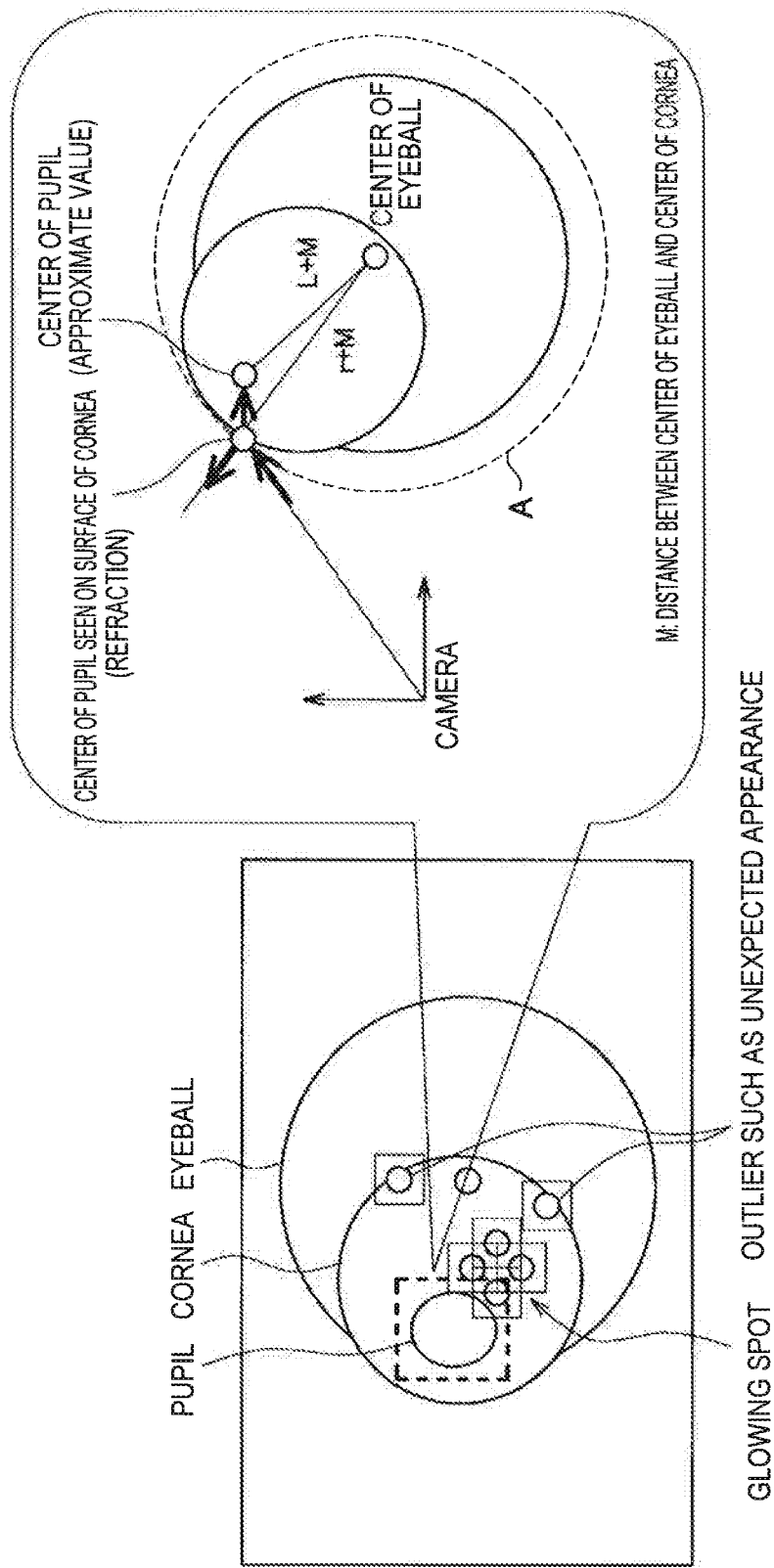
FIG. 4 is an explanatory diagram for describing an example of the processing according to the information processing method according to the present embodiment.

FIG. 4 is an explanatory diagram for describing an example of the processing according to the information processing method according to the present embodiment, and shows an overview of processing for the estimation of the position of the center of the pupil.

A of FIG. 4 shows a sphere with the center at the position of the center of the eyeball and a radius of r+M. Here, r represents the radius of the cornea, and M represents the distance between the center of the eyeball and the center of the cornea (hereinafter, this similarly applies to the description of the other drawings). L shown in FIG. 4 represents the distance between the center of the cornea and the center of the pupil (hereinafter, this similarly applies to the description of the other drawings). The radius r of the cornea, the distance M between the center of the eyeball and the center of the cornea, and the distance L between the center of the cornea and the center of the pupil correspond to examples of the information concerning the eye according to the present embodiment.

Here, the radius r of the cornea and the distance L between the center of the cornea and the center of the pupil may be a set fixed value, for example. The distance M between the center of the eyeball and the center of the cornea may be a value estimated on the basis of the position of the center of the eyeball estimated by the processing of (1) mentioned above, or may be a set fixed value, for example. The estimation of the distance M between the center of the eyeball and the center of the cornea may be performed at an arbitrary timing after the position of the center of the eyeball is estimated in the processing of (1) mentioned above.

The information processing apparatus according to the present embodiment assumes that the pupil is refracted on the surface of the sphere shown by A of FIG. 4, and calculates the three-dimensional position of the center of the pupil using Snell's law, for example.

(2-2) Estimation of Position of Center of Cornea

The information processing apparatus according to the present embodiment estimates, as the position of the center of the cornea, a position on the line segment connecting the position of the center of the eyeball estimated by the processing of (1) mentioned above and the position of the center of the pupil estimated by the processing of (2-1) mentioned above, for example.

Figure 5:
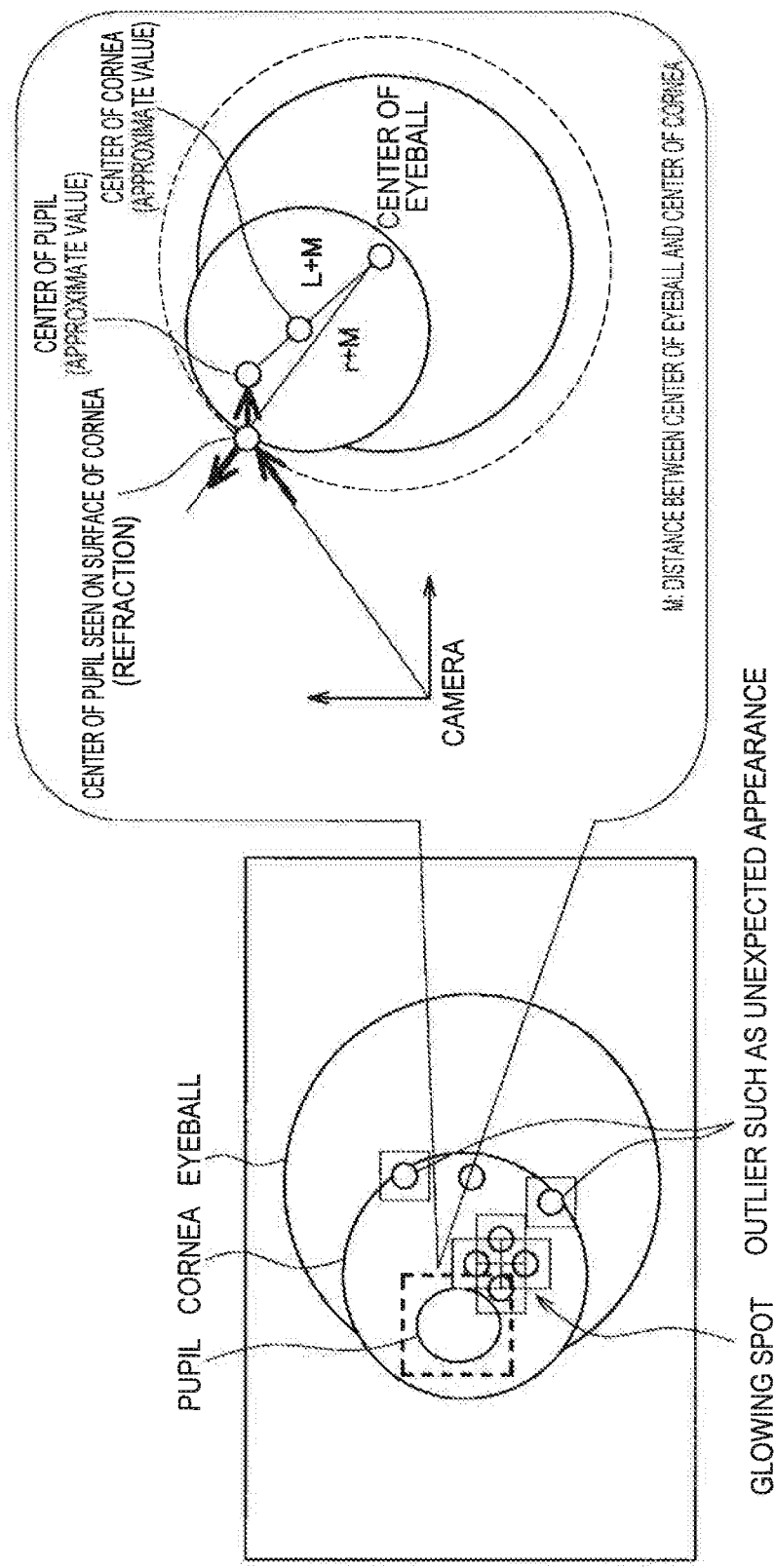
FIG. 5 is an explanatory diagram for describing an example of the processing according to the information processing method according to the present embodiment.

FIG. 5 is an explanatory diagram for describing an example of the processing according to the information processing method according to the present embodiment, and shows an overview of processing for the estimation of the position of the center of the cornea.

The information processing apparatus according to the present embodiment estimates, as the position of the center of the cornea, point (x, y, z) that divides the line segment connecting the estimated position of the center of the pupil and the estimated position of the center of the eyeball to L:M on the basis of the distance L between the center of the cornea and the center of the pupil (an example of the information concerning the eye) and the distance M between the center of the eyeball and the center of the cornea (an example of the information concerning the eye), for example.

(3) Estimation of Position of Candidate for Corneal Reflection Image

The information processing apparatus according to the present embodiment estimates the position of a candidate for the corneal reflection image on the basis of the position of the center of the cornea estimated by the processing of (2) mentioned above. In the following, the position of a candidate for the corneal reflection image may be referred to as "the position of a candidate for the glowing spot."

The information processing apparatus according to the present embodiment estimates the position of a candidate for the corneal reflection image on the basis of the estimated position of the center of the cornea, information concerning the eye, and the position of a light source, for example.

Figure 6:
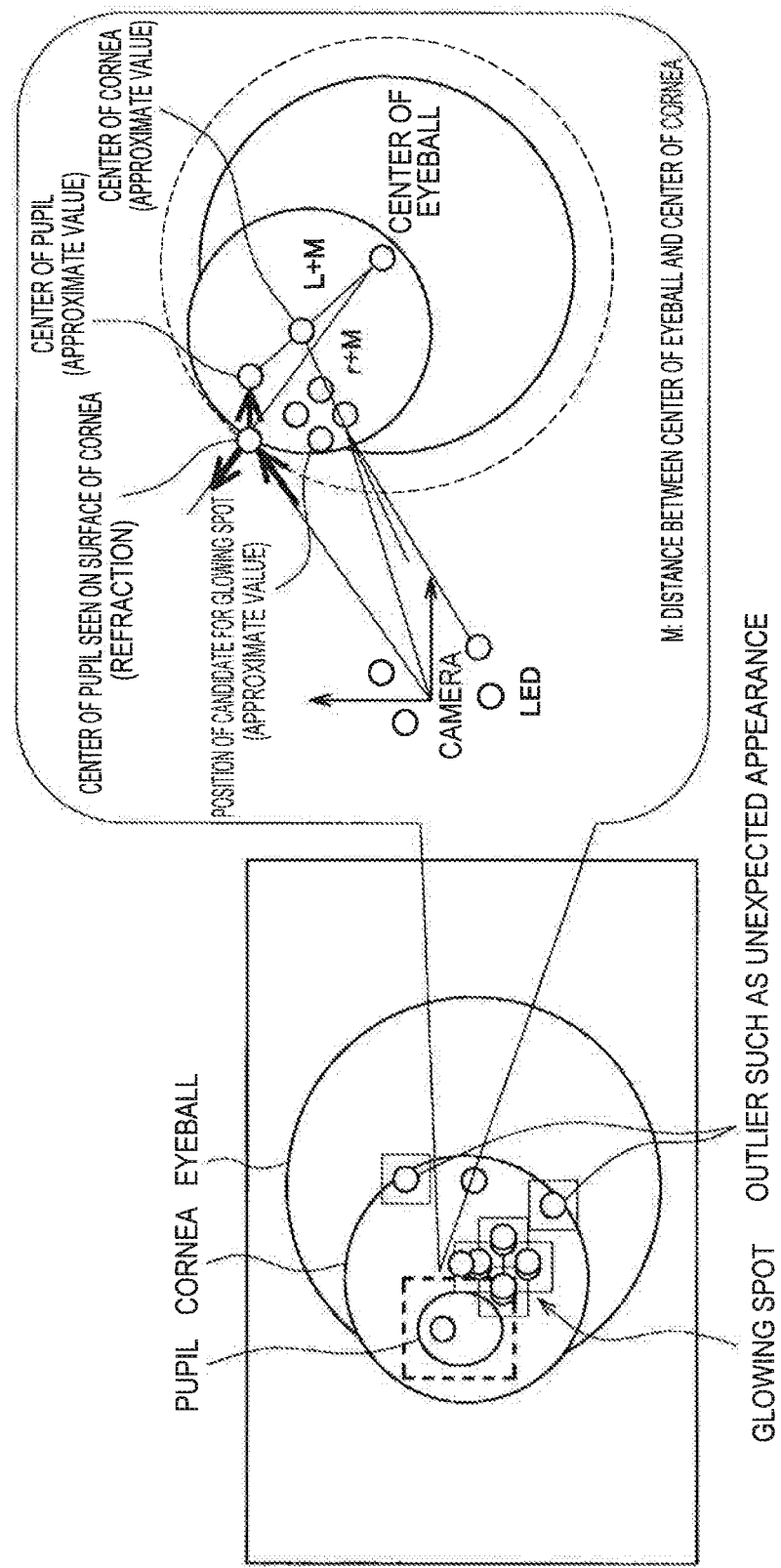
FIG. 6 is an explanatory diagram for describing an example of the processing according to the information processing method according to the present embodiment.

FIG. 6 is an explanatory diagram for describing an example of the processing according to the information processing method according to the present embodiment, and shows an overview of processing for the estimation of the position of a candidate for the corneal reflection image.

The information processing apparatus according to the present embodiment finds the position (x, y, z) of the reflection of the light of a light source using the law of reflection on the basis of the estimated position of the center of the cornea, the radius r of the cornea (an example of the information concerning the eye), and data showing the placement of an IR LED with respect to the imaging device (an example of the information showing the position of the light source), for example. Then, the information processing apparatus according to the present embodiment projects the found position (x, y, z) of reflection on the image plane, and thereby estimates the position of a candidate for the corneal reflection image (for example, a position expressed by the (u, v) coordinates).

The processing for the estimation of the position of a candidate for the corneal reflection image will now be described more specifically.

Figure 7:
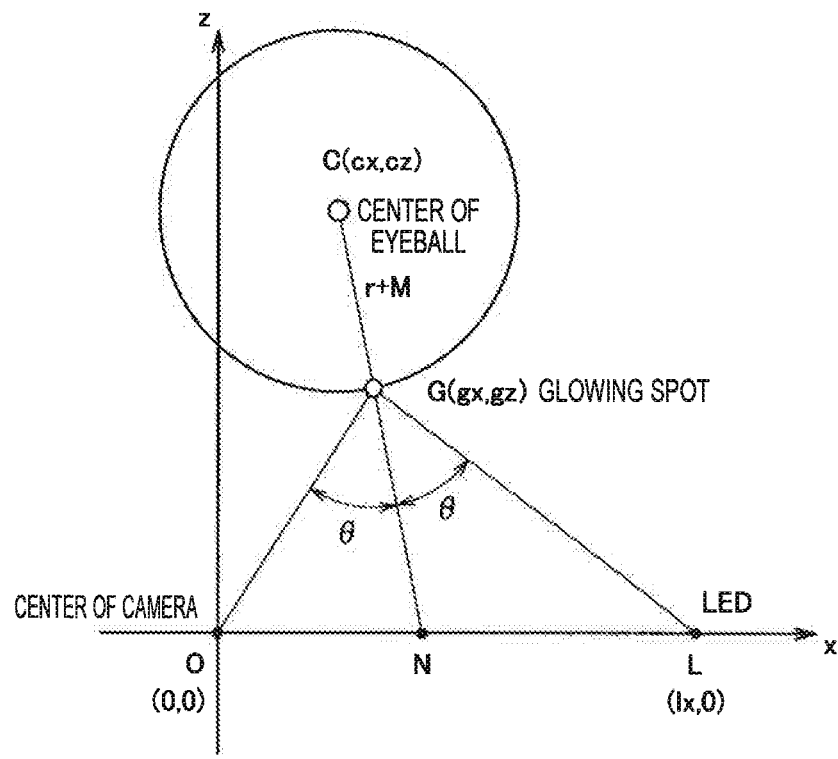
FIG. 7 is an explanatory diagram for describing an example of the processing according to the information processing method according to the present embodiment.

FIG. 7 is an explanatory diagram for describing an example of the processing according to the information processing method according to the present embodiment, and shows an overview of processing for the estimation of the position of a candidate for the corneal reflection image. O(0, 0) shown in FIG. 7 indicates the center of the camera, and L shown in FIG. 7 indicates the position of one IR LED (an example of the light source). C(cx, cy) shown in FIG. 7 indicates the position of the center of the eyeball, and G(gx, gz) shown in FIG. 7 indicates the position of a glowing spot.

According to the law of spherical reflection, the center of the camera, the glowing spot, the IR LED, and the center of the eyeball exist on the same plane. As shown in FIG. 7, on the plane mentioned above, an x-axis is set in the direction passing through the center of the camera and the position of the IR LED, and a z-axis is set in a direction orthogonal to the x-axis and toward near the position of the center of the eyeball, for example.

Here, the angle of incidence and the angle of reflection of the light of the IR LED (an example of the light of the light source) are equal, and thus θ=angle OGN=angle LGN. G(gx, gz) is a point on the circumference of a circle with the center at the center of the eyeball C(cx, cy) and a radius of r+M.

The information processing apparatus according to the present embodiment solves the nonlinear simultaneous equations shown in Mathematical Formula 5 below for gx and gy, and converts the solution to the directional vector of the glowing spot (the corneal reflection image) in the camera coordinate system; thereby, finds the position (u, v) of a candidate for the corneal reflection image, for example.

Mathematical Formula 5

$$\begin{cases} \dfrac{\vec{GO} \cdot \vec{CG}}{|\vec{GO}| \times |\vec{CG}|} = \dfrac{\vec{GL} \cdot \vec{CG}}{|\vec{GL}| \times |\vec{CG}|} \\ (gx - cx)^2 + (gz - cz)^2 = (r + M)^2 \end{cases}$$ [Math. 5]

(4) Detection of Corneal Reflection Image

The information processing apparatus according to the present embodiment detects a corneal reflection image from a captured image on the basis of the position of the candidate for the corneal reflection image estimated by the processing of (3) mentioned above.

Figure 8:
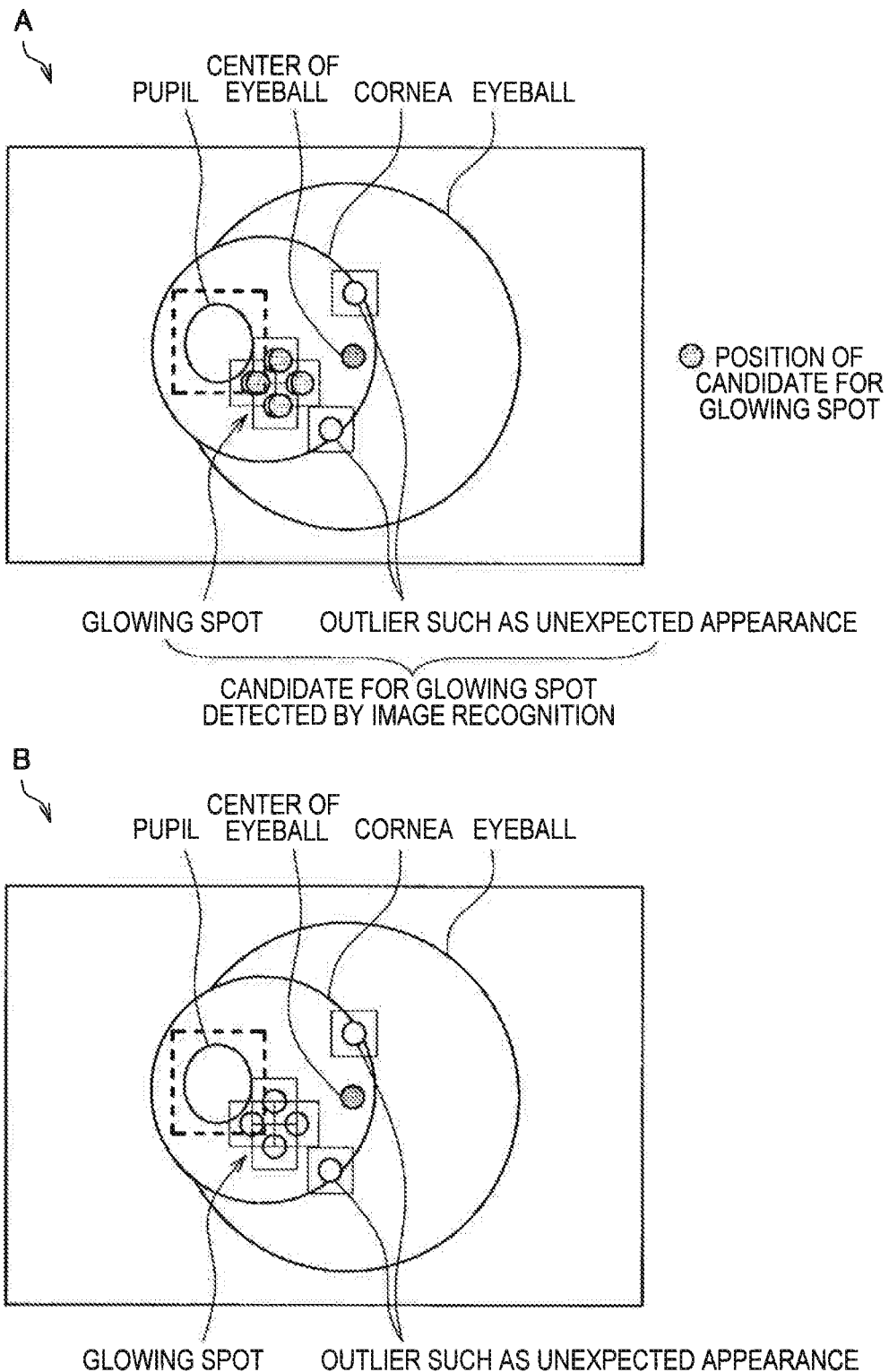
FIG. 8 is an explanatory diagram for describing an example of the processing according to the information processing method according to the present embodiment.

FIG. 8 is an explanatory diagram for describing an example of the processing according to the information processing method according to the present embodiment, and shows an overview of processing for the detection of a corneal reflection image.

The information processing apparatus according to the present embodiment detects a corneal reflection image from a captured image using, as constraints, "the distance between the position of the candidate for the corneal reflection image detected by image recognition by the processing according to the second step described in (ii) mentioned above and the position of the candidate for the corneal reflection image estimated by the processing of (3) mentioned above," "the slopes in the u-direction and the v-direction between corneal reflection images corresponding to the positional relationships between a plurality of IR LEDs," etc., for example.

The information processing apparatus according to the present embodiment performs detection processing including the processing described in (1) to (4) mentioned above as processing according to the information processing method according to the present embodiment, for example.

By detection processing according to the present embodiment being performed, the range of existence of corneal reflection images for detecting a corneal reflection image can be significantly reduced as compared to the case where the one method for detecting a corneal reflection image from a captured image described above is used.

Thus, by performing detection processing according to the present embodiment, the information processing apparatus according to the present embodiment can detect a corneal reflection image from a captured image with better accuracy than in the case where the one method for detecting a corneal reflection image from a captured image described above is used.

Furthermore, the pieces of processing described in (iv) mentioned above to (vii) mentioned above are performed using a corneal reflection image detected by detection processing according to the present embodiment; thereby, the accuracy of estimation of a vector corresponding to the eye gaze (the optical axis vector, or the eye gaze vector in which the optical axis vector is corrected) can be enhanced as compared to the case where a corneal reflection image is detected using the one method for detecting a corneal reflection image from a captured image described above.

The processing according to the information processing method according to the present embodiment is not limited to the detection processing mentioned above. For example, the information processing apparatus according to the present embodiment may further perform the processing of (I) to the processing of (IV) below as processing according to the information processing method according to the present embodiment.

(I) Processing for Detection of Vector Corresponding to Eye Gaze

The information processing apparatus according to the present embodiment performs the processing of (iv) mentioned above to the processing of (vi) mentioned above to detect the optical axis vector (an example of the vector corresponding to the eye gaze) using the position of a corneal reflection image detected in the detection processing mentioned above, for example.

The information processing apparatus according to the present embodiment detects the optical axis vector on the basis of the position of a corneal reflection image detected in the detection processing mentioned above, information concerning the eye, and the position of a light source, for example.

More specifically, the information processing apparatus according to the present embodiment detects the optical axis vector using two or more of the position of the center of the cornea identified by the processing of (iv) mentioned above, the position of the center of the pupil identified by the processing of (v) mentioned above, and the position of the center of the eyeball estimated in the detection processing mentioned above, for example. Here, the position of the center of the cornea, the position of the center of the pupil, and the position of the center of the eyeball exist on a straight line. Thus, the information processing apparatus according to the present embodiment detects, as the optical axis vector, a vector directed toward the outside of the eyeball and connecting two points among the position of the center of the cornea, the position of the center of the pupil, and the position of the center of the eyeball, for example.

The processing for the detection of a vector corresponding to the eye gaze according to the present embodiment is not limited to the example described above.

For example, the information processing apparatus according to the present embodiment may use the position of a corneal reflection image detected in the detection processing mentioned above to perform the processing of (iv) mentioned above to the processing of (vii) mentioned above, and can thereby detect the eye gaze vector in which the optical axis vector is corrected (an example of the vector corresponding to the eye gaze). The information processing apparatus according to the present embodiment corrects the optical axis vector by the processing of (iv) mentioned above to (vi) mentioned above using a set offset value, and thereby detects the eye gaze vector, for example.

(II) Processing Using Vector Corresponding to Eye Gaze

The information processing apparatus according to the present embodiment may perform processing using a vector corresponding to the eye gaze detected in the processing of (I) mentioned above (the optical axis vector or the eye gaze vector in which the optical axis vector is corrected; this similarly applies hereinafter), or a vector corresponding to the eye gaze that is detected by a processing similar to the processing of (1) mentioned above in an external device, for example.

The processing using a vector corresponding to the eye gaze according to the present embodiment may be processing that detects a change in the wearing state of the device usable by being worn on the user's head according to the present embodiment. In the following, the processing that detects a change in the wearing state of the device usable by being worn on the user's head according to the present embodiment may be referred to as "wearing slippage detection processing" or "wearing slippage detection."

In the case where wearing slippage detection processing is performed as processing using a vector corresponding to the eye gaze, the information processing apparatus according to the present embodiment detects a change in the wearing state on the basis of the distance between the optical axis vector detected at time t (a first time point) and the position of the center of the eyeball estimated at a certain time point in the period up to time t−1 (a second time point before the first time point), for example.

In the case where the wearing state of the device usable by being worn on the user's head according to the present embodiment does not change, the optical axis vector does not change, and the position of the center of the cornea, the position of the center of the pupil, and the position of the center of the eyeball exist on a straight line, as described above. Thus, the information processing apparatus according to the present embodiment calculates the distance between the optical axis vector detected at time t and the position of the center of the eyeball estimated at a certain time point in the period up to time t−1; when the calculated distance is found to be larger than a set threshold (or when the distance is found to be not less than the threshold), the information processing apparatus assesses that a change in the wearing state has occurred, and thereby detects a change in the wearing state, for example.

The information processing apparatus according to the present embodiment may detect a change in the wearing state also when it is assessed that a change in the wearing state has occurred successively in a plurality of frames, for example.

When a change in the wearing state is detected, the information processing apparatus according to the present embodiment performs the detection processing mentioned above again, and initializes the position of the center of the eyeball etc., for example. The information processing apparatus according to the present embodiment may also use the result of the above-mentioned detection processing performed again and perform the processing of (1) mentioned above (processing for the detection of a vector corresponding to the eye gaze), for example.

The processing on the occasion when a change in the wearing state is detected is not limited to the example described above.

For example, when a change in the wearing state is detected, the information processing apparatus according to the present embodiment may cause the fact that a change in the wearing state is detected to be notified to the user. The information processing apparatus according to the present embodiment causes a display device to perform visual notification by causing a character or an image to be displayed, or causes a sound output device to perform auditory notification by causing sound (including music) to be outputted; thereby, causes the fact that a change in the wearing state is detected to be notified to the user, for example. The information processing apparatus according to the present embodiment causes the fact that a change in the wearing state is detected to be notified to the user by causing a display device or a sound output device to transmit a control signal or data concerning notification to a communication unit (described later) included in the information processing apparatus according to the present embodiment or to an external communication device, for example.

Further, when a change in the wearing state is detected, the information processing apparatus according to the present embodiment may perform various pieces of processing such as lowering the degree of confidence that is supplementary information of the result of detection of a vector corresponding to the eye gaze from a set standard value or adjusting the amount of offset (the offset value) for correcting the optical axis vector, for example. Here, the standard value of the degree of confidence mentioned above may be a fixed value set in advance, or may be a variable value set by any method that can set the degree of confidence in accordance with the result of detection of a vector corresponding to the eye gaze.

The information processing apparatus according to the present embodiment performs wearing slippage processing like the above as processing using a vector corresponding to the eye gaze according to the present embodiment, for example.

The processing using a vector corresponding to the eye gaze according to the present embodiment is not limited to the wearing slippage processing mentioned above.

The information processing apparatus according to the present embodiment may perform any processing that can be implemented using a vector corresponding to the eye gaze, such as the control of an application in accordance with the position on the display screen of the eye gaze that is identified using a vector corresponding to the eye gaze detected in the processing of (I) mentioned above.

(III) Image Recognition Processing on Captured Image

The information processing apparatus according to the present embodiment may also perform image recognition processing on a captured image and recognize the pupil and a candidate for the corneal reflection image from the captured image, for example. The information processing apparatus according to the present embodiment recognizes the pupil and a candidate for the corneal reflection image from a captured image by performing the processing of (i) mentioned above and the processing of (ii) mentioned above, for example.

In the case where the information processing apparatus according to the present embodiment performs image recognition processing on a captured image, the information processing apparatus according to the present embodiment detects a corneal reflection image using the result of image recognition processing on the captured image in the detection processing mentioned above.

(IV)

The information processing apparatus according to the present embodiment may further perform two or more of the processing of (I) mentioned above (processing for the detection of a vector corresponding to the eye gaze) to the processing of (III) mentioned above (image recognition processing on a captured image) as processing according to the information processing method according to the present embodiment, for example.

Figure 9:
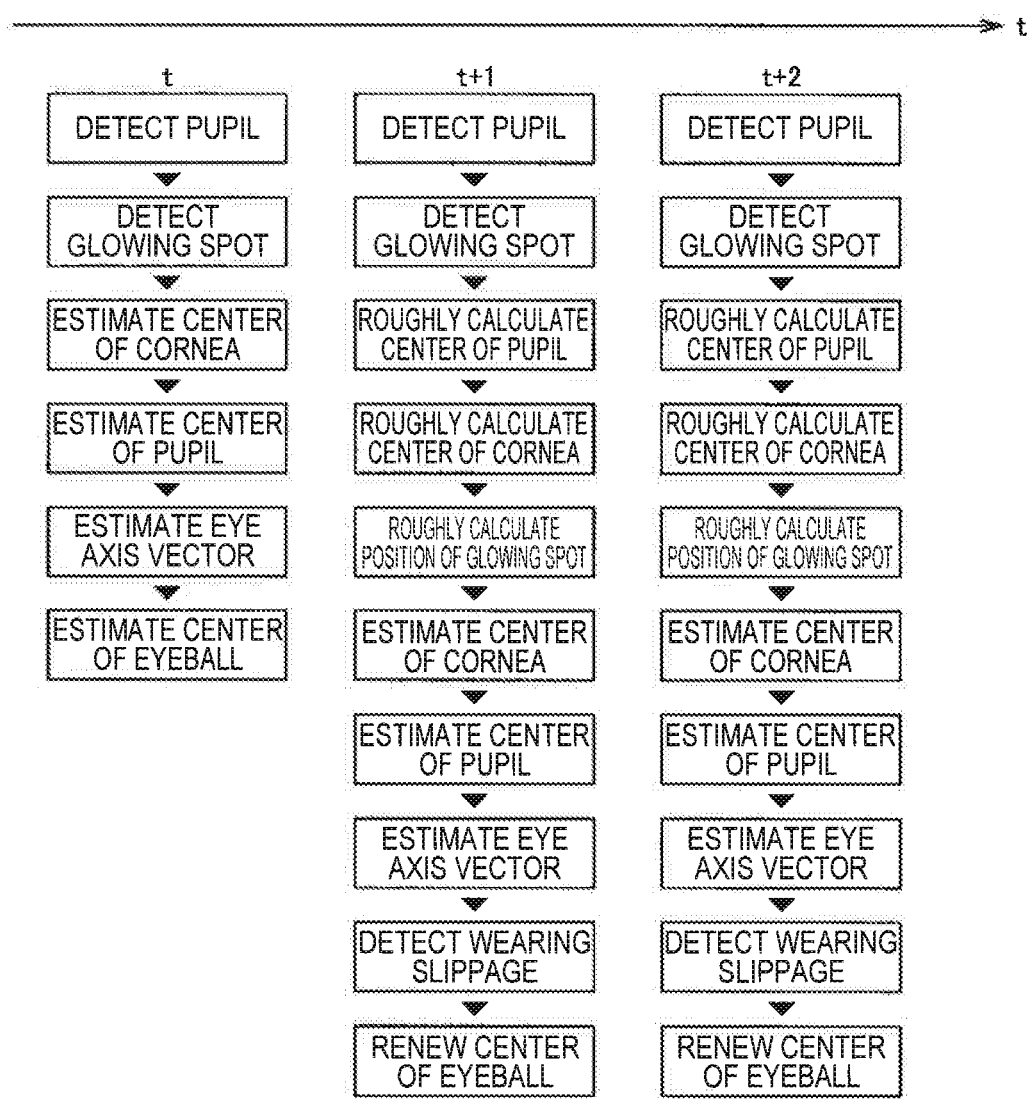
FIG. 9 is an explanatory diagram for describing an example of the processing according to the information processing method according to the present embodiment.

FIG. 9 is an explanatory diagram for describing an example of the processing according to the information processing method according to the present embodiment. FIG. 9 shows an example of the processing performed at each time point in the case where the information processing apparatus according to the present embodiment performs, as processing according to the information processing method according to the present embodiment, the detection processing mentioned above, the processing of (I) mentioned above (processing for the detection of a vector corresponding to the eye gaze), the processing of (II) mentioned above (processing using a vector corresponding to the eye gaze), and the processing of (III) mentioned above (image recognition processing on a captured image).

At time t shown in FIG. 9, the information processing apparatus according to the present embodiment performs processing using the one method for detecting a corneal reflection image from a captured image described above, for example. At times t+1 and t+2 shown in FIG. 9, the information processing apparatus according to the present embodiment performs processing using the information processing method according to the present embodiment.

Thus, in the case where the processing shown in FIG. 9 is performed, with the lapse of time, a corneal reflection image can be detected from a captured image with higher accuracy, for example.

Further, in the example shown in FIG. 9, the information processing apparatus according to the present embodiment performs wearing slippage processing as the processing of (II) mentioned above (processing using a vector corresponding to the eye gaze). In the example shown in FIG. 9, when a change in the wearing state is detected by wearing slippage processing, the information processing apparatus according to the present embodiment performs the processing from time t shown in FIG. 9 again, for example.

The information processing apparatus according to the present embodiment performs "the detection processing mentioned above" or "the detection processing mentioned above and one of the processing of (I) to the processing of (IV) mentioned above" as processing according to the information processing method according to the present embodiment, for example.

"The detection processing mentioned above" and "the detection processing mentioned above and one of the processing of (I) to the processing of (IV) mentioned above" are pieces of processing divided from the processing according to the information processing method according to the present embodiment, for the sake of convenience. Hence, in the processing according to the information processing method according to the present embodiment, "the detection processing mentioned above" can be seen as two or more pieces of processing (in an arbitrary way of division), for example. Further, in the processing according to the information processing method according to the present embodiment, "the detection processing mentioned above and one of the processing of (I) to the processing of (IV) mentioned above" can be seen as one processing, or "the detection processing mentioned above and one of the processing of (I) to the processing of (IV) mentioned above" can be seen as two or more pieces of processing (in an arbitrary way of division), for example.

[3] Effects Exhibited by Processing According to Information Processing Method According to the Present Embodiment being Performed By performing processing according to the information processing method according to the present embodiment, the information processing apparatus according to the present embodiment can exhibit effects like those shown in (a) to (e) below, for example. The effect exhibited by processing according to the information processing method according to the present embodiment being performed is not limited to the examples shown below, as a matter of course.

(a) The accuracy of removal of an outlier of the corneal reflection image (glowing spot) and the accuracy of making an association with an IR LED (an example of the light source) can be improved.

(b) The accuracy of detection of a vector corresponding to the eye gaze can be improved by virtue of the effect shown in (a) mentioned above.

(c) A change in the wearing state of the device usable by being worn on the user's head according to the present embodiment can be detected using the result of processing according to the information processing method according to the present embodiment (for example, a vector corresponding to the eye gaze detected and the position of the center of the eyeball estimated).

(d) The degree of confidence of the vector corresponding to the eye gaze can be set by, for example, utilizing the result of detection of a change in the wearing state of (c) mentioned above, etc.

(e) Various pieces of processing (e.g., notification, the adjustment of the amount of offset, etc.) using, for example, the result of detection of a change in the wearing state of (c) mentioned above can be performed.

(Information Processing Apparatus According to the Present Embodiment)

Next, an example of the configuration of the information processing apparatus according to the present embodiment that can perform the processing according to the information processing method according to the present embodiment described above is described.

Figure 10:
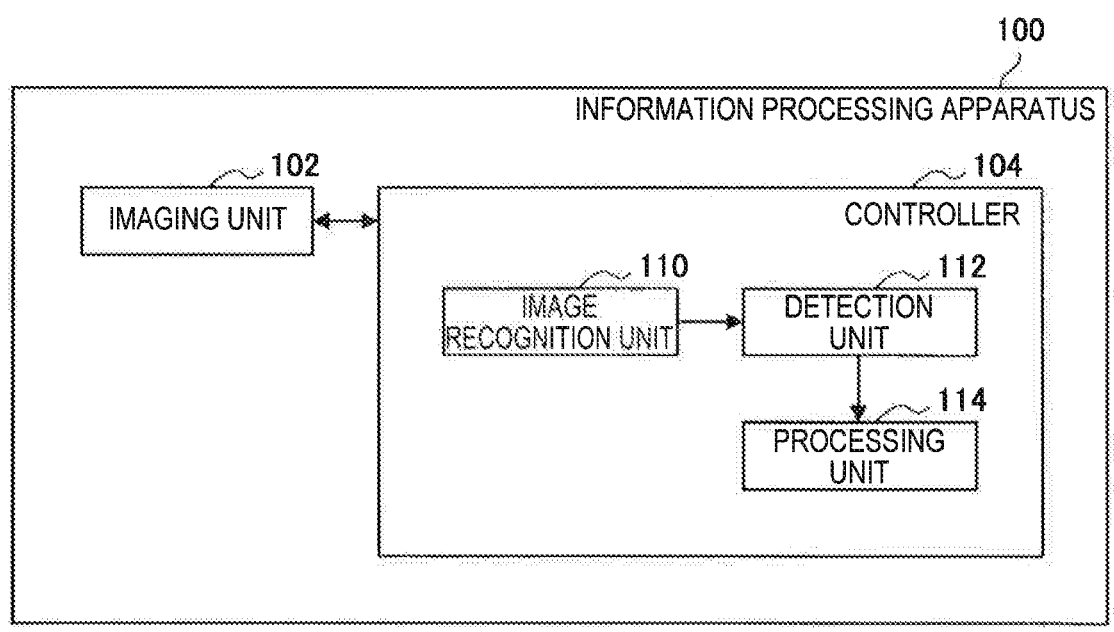
FIG. 10 is a block diagram showing an example of the configuration of an information processing apparatus according to the present embodiment.

FIG. 10 is a block diagram showing an example of the configuration of an information processing apparatus 100 according to the present embodiment. The information processing apparatus 100 includes an imaging unit 102 and a controller 104, for example.

The information processing apparatus 100 may include a read-only memory (ROM, not illustrated), a random access memory (RAM, not illustrated), a storage unit (not illustrated), a communication unit for performing communication with an external device wirelessly or via wire (not illustrated), an operation unit that the user can operate (not illustrated), a display unit that displays various screens on a display screen (not illustrated), etc., for example. The information processing apparatus 100 connects the components mentioned above by means of a bus as a data transfer path, for example.

The ROM (not illustrated) stores control data such as a program and operation parameters used by the controller 104. The RAM (not illustrated) temporarily stores a program and the like executed by the controller 104.

The storage unit (not illustrated) is a storage means included in the information processing apparatus 100, and stores various data such as data for the information processing method according to the present embodiment such as information concerning the eye, image data showing captured images, and applications, for example. In the storage unit (not illustrated), information concerning the eye such as the radius of the cornea, the distance between the center of the eyeball and the center of the cornea, and the distance between the center of the cornea and the center of the pupil is stored for each user, for example. Further, in the storage unit (not illustrated), dictionary data for the detection of a corneal reflection image and the pupil may be stored as data for the information processing method according to the present embodiment, for example.

Here, a magnetic recording medium such as a hard disk and a nonvolatile memory such as a flash memory may be presented as examples of the storage unit (not illustrated). The storage unit (not illustrated) may be attachable to/detachable from the information processing apparatus 100.

Examples of the communication unit (not illustrated) include a communication interface described later. Examples of the operation unit (not illustrated) include an operation input device described later, and examples of the display unit (not illustrated) include a display device described later.

[Example of Hardware Configuration of Information Processing Apparatus 100]

FIG. 9 is an explanatory diagram of an example of the hardware configuration of the information processing apparatus 100 according to the present embodiment. For example, the information processing apparatus 100 includes an MPU 150, a ROM 152, a RAM 154, a recording medium 156, an input/output interface 158, an operation input device 160, a display device 162, a communication interface 164, an imaging device 166 and a IR LED 168. In addition, the information processing apparatus 100, for example, connects the respective components using a bus 170 serving as a data transfer path.

The MPU 150 functions as, for example, one or two or more processors configured of an arithmetic circuit such as a micro-processing unit (MPU), and the controller 104 that is configured of various processing circuits etc. and controls the entire information processing apparatus 100. Further, the MPU 150 plays the roles of an image recognition unit 110, a detection unit 112, and a processing unit 114 described later in the information processing apparatus 100, for example.

The ROM 152 stores control data such as a program and operation parameters used by the MPU 150. The RAM 154 temporarily stores, for example, a program and the like executed by the MPU 150.

The recording medium 156 functions as a storage unit (not illustrated), and stores various data such as data for the information processing method according to the present embodiment such as information concerning the eye, image data showing captured images, and applications, for example.

A magnetic recording medium such as a hard disk and a nonvolatile memory such as a flash memory may be presented as examples of the recording medium 156. The storage unit (not illustrated) may be attachable to/detachable from the information processing apparatus 100.

The input/output interface 158 is connected to, for example, the operation input device 160 and the display device 162. The operation input device 160 functions as the operation unit (not illustrated) and the display device 162 functions as the display unit (not illustrated). Here, a universal serial bus (USB) terminal, a digital visual interface (DVI) terminal, a High-Definition Multimedia Interface (HDMI) (registered trademark) terminal and various processing circuits may be presented as examples of the input/output interface 158.

The operation input device 160 is included in the information processing apparatus 100 and connected to the input/output interface 158 inside the information processing apparatus 100. For example, a button, direction keys, a rotary type selector such as a jog dial or a combination thereof may be presented as an example of the operation input device 160.

The display device 162 is included in the information processing apparatus 100 and connected to the input/output interface 158 in the information processing apparatus 100. For example, a liquid crystal display and an organic electroluminescence display (or an organic light emitting diode (OLED) display) may be presented as examples of the display device 162.

The input/output interface 158 may be connected to external devices of the information processing apparatus 100, such as the operation input device (e.g., keyboard and mouse), the display device and the imaging device. In addition, the display device 162 may be a display device that may be manipulated by the user, such as a touch device.

The communication interface 164 is a communication means included in the information processing apparatus 100 and serves as a communication unit (not illustrated) for performing wireless or wired communication with an external apparatus (or external device), such as an external imaging device, an external display device and an external device usable by being worn on the user's head according to the present embodiment, via a network (or directly). For example, a communication antenna and radio frequency (RF) circuit (wireless communication), an IEEE 802.15.1 port and transmission/reception circuit (wireless communication), an IEEE 802.11 port and transmission/reception circuit (wireless communication) or a local area network (LAN) terminal and transmission/reception circuit (wired communication) may be presented as examples of the communication interface 164. In addition, the communication unit (not illustrated) may have a configuration corresponding to arbitrary standards for communication, such as a Universal Serial Bus (USB) terminal and transmission/reception circuit, or a configuration for communicating with an external apparatus via a network.

For example, a network according to the present embodiment may be a wired network such as a LAN and a wide area network (WAN), a wireless network such as a wireless local area network (WLAN) and a wireless wide area network (WWAN) via a base station or the Internet using a communication protocol such as the transmission control protocol/Internet protocol (TCP/IP).

The imaging device 166 is an imaging means included in the information processing apparatus 100, and functions as the imaging unit 102 that generates an image (a captured image) by imaging. The imaging device 166 is configured of one or two or more imaging devices that image one eye of the user or both eyes of the user, for example. The imaging device 166 is provided in a position that allows an eye irradiated with the light from a light source such as an IR LED to be imaged, for example.

In the case where the imaging device 166 is provided in the information processing apparatus 100, processing according to the information processing method according to the present embodiment can be performed on the basis of a captured image generated by imaging in the imaging device 166, for example.

The imaging device 166 includes, for example, a lens/imaging element and a signal processing circuit. The lens/imaging element includes, for example, an optical lens and an image sensor using a plurality of imaging elements such as complementary oxide semiconductors (CMOSs). The signal processing circuit includes, for example, an automatic gain control (AGC) circuit and an analog-to-digital converter (ADC), and converts an analog signal generated by the imaging element into a digital signal (image data). The signal processing circuit performs various processes related to, for example, a RAW processing. In addition, the signal processing circuit may perform various signal processes such as white balance adjustment, color tone correction, gamma correction, YCbCr conversion and edge emphasizing.

The IR LED 168 is a light source included in the information processing apparatus 100, and is composed of a plurality of IR LEDs. The IR LED 168 is provided in a position that allows light to be applied to the user's eye, for example. As described above, the light source included in the information processing apparatus 100 is not limited to an IR LED, as a matter of course.

Figure 11:
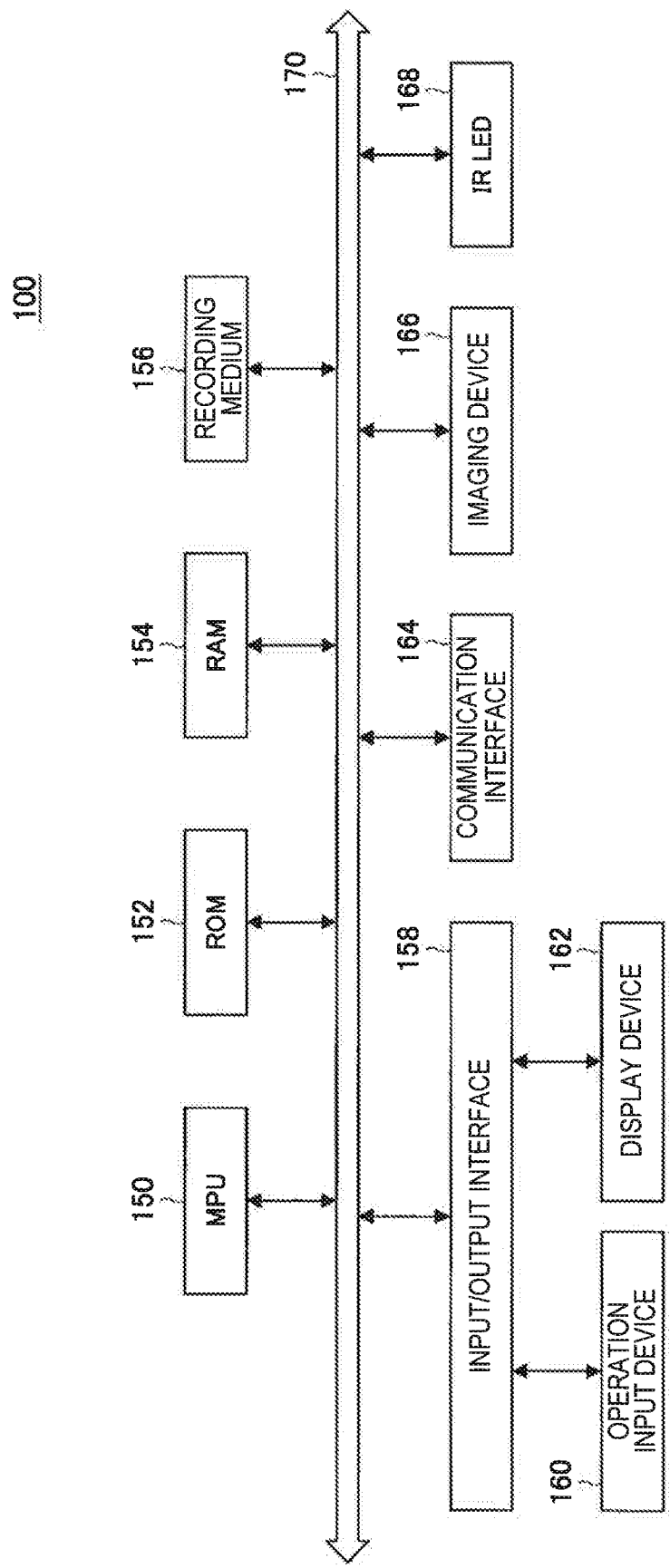
FIG. 11 is an explanatory diagram showing an example of the hardware configuration of the information processing apparatus according to the present embodiment.

The information processing apparatus 100 performs processing according to the information processing method according to the present embodiment using the configuration illustrated in FIG. 11. The hardware configuration of the information processing apparatus 100 according to the present embodiment is not limited to the configuration illustrated in FIG. 11.

For example, in the case of processing a captured image according to the present embodiment acquired from an external device usable by being worn on the user's head according to the present embodiment or the like, the information processing apparatus 100 may have a configuration in which one of the imaging device 166 and the IR LED 168 is not provided or neither of them is provided.

In the case where the information processing apparatus 100 has a configuration in which processing is performed in a stand-alone manner, the information processing apparatus 100 may not include the communication interface 164, for example. Further, the information processing apparatus 100 may have a configuration not including the recording medium 156, the operation input device 160, and/or the display device 162.

An example of the configuration of the information processing apparatus 100 according to the present embodiment will now be described with reference to FIG. 2 again. The imaging unit 102 generates a captured image in which an eye irradiated with the light from a light source is imaged (a captured image of the present embodiment). Examples of the imaging unit 102 include the imaging device 166.

The controller 104 is configured of, for example, an MPU or the like, and plays the role of controlling the entire information processing apparatus 100. Further, the controller 104 includes the image recognition unit 110, the detection unit 112, and the processing unit 114, and plays the role of leadingly performing processing according to the information processing method according to the present embodiment, for example. Here, FIG. 10 shows an example of the configuration in the case where the controller 104 performs the detection processing mentioned above and the processing of (IV) mentioned above as processing according to the information processing method according to the present embodiment.

The image recognition unit 110 plays the role of leadingly performing the processing of (II) mentioned above (image recognition processing on a captured image), and recognizes the pupil and a candidate for the corneal reflection image from a captured image. The image recognition unit 110 recognizes the pupil and a candidate for the corneal reflection image from a captured image by performing the processing of (i) mentioned above and the processing of (ii) mentioned above, for example.

The detection unit 112 plays the role of leadingly performing the detection processing mentioned above, and detects a corneal reflection image from a captured image. The detection unit 112 detects a corneal reflection image by performing the processing of (1) (the estimation of the position of the center of the eyeball) to the processing of (4) (the detection of a corneal reflection image) mentioned above, for example.

The detection unit 112 may further perform the processing of (I) mentioned above (processing for the detection of a vector corresponding to the eye gaze) using the result of detection of a corneal reflection image.

The processing unit 114 plays the role of leadingly performing the processing of (II) mentioned above (processing using a vector corresponding to the eye gaze), and performs processing using a vector corresponding to the eye gaze (the optical axis vector or the eye gaze vector in which the optical axis vector is corrected). The processing unit 114 performs any processing that can be implemented using a vector corresponding to the eye gaze, such as wearing slippage processing.

The controller 104 includes the image recognition unit 110, the detection unit 112, and the processing unit 114, and thereby leadingly performs processing according to the information processing method according to the present embodiment, for example.

The information processing apparatus 100 performs processing according to the information processing method according to the present embodiment (for example, the detection processing mentioned above and the processing of (IV) mentioned above) by means of the configuration shown in FIG. 10, for example.

Thus, the information processing apparatus 100 can detect a corneal reflection image from a captured image by means of the configuration shown in FIG. 10, for example.

Furthermore, by means of the configuration shown in FIG. 10, the information processing apparatus 100 can exhibit an effect that is brought out by processing according to the information processing method according to the present embodiment like that described above being performed, for example.

The configuration of the information processing apparatus according to the present embodiment is not limited to the configuration shown in FIG. 10.

For example, the information processing apparatus according to the present embodiment may include one or two or more of the image recognition unit 110, the detection unit 112, and the processing unit 114 shown in FIG. 10 separately from the controller 104 (for example, configure these components using other processing circuits).

In the case where, for example, the processing of (III) mentioned above (image recognition processing on a captured image) is performed in an external device and processing is performed using the processing result of the external device, the information processing apparatus according to the present embodiment may not include the image recognition unit 110.

In the case where, for example, the processing of (II) mentioned above (processing using a vector corresponding to the eye gaze) is performed in an external device, the information processing apparatus according to the present embodiment may not include the processing unit 114.

As described above, "the detection processing mentioned above" and "the detection processing mentioned above and one of the processing of (I) to the processing of (IV) mentioned above" are pieces of processing divided from the processing according to the information processing method according to the present embodiment, for the sake of convenience. Thus, the configuration for implementing processing according to the information processing method according to the present embodiment is not limited to the image recognition unit 110, the detection unit 112, and the processing unit 114 shown in FIG. 10, and may be a configuration in accordance with the way of division of the processing according to the information processing method according to the present embodiment.

Hereinabove, the present embodiment is described using an information processing apparatus, but the present embodiment is not limited to this form. The present embodiment may be used for various devices that can process images, such as a device usable by being worn on the user's head such as an eyewear and an HMD, a computer such as a personal computer (PC) and a server, a communication device such as a mobile phone and a smartphone, and a tablet device. Further, the present embodiment may be used for one or two or more integrated circuits (IC) that can be incorporated into a device like the above, for example.

Further, the information processing apparatus according to the present embodiment may be used for a system that is composed of one or two or more devices and is designed to be connected to a network (or to perform communication between devices), such as for cloud computing. In other words, the information processing apparatus according to the present embodiment described above may be configured as an information processing system composed of a plurality of devices, for example.

(Program According to the Present Embodiment)

A program for causing a computer to function as the information processing apparatus according to the present embodiment (for example, a program capable of executing processing according to the information processing method according to the present embodiment such as "the detection processing mentioned above" or "the detection processing mentioned above and one of the processing of (I) to the processing of (IV) mentioned above") may be executed by a processor or the like in a computer, and thereby a corneal reflection image can be detected from a captured image.

Further, by a program for causing a computer to function as the information processing apparatus according to the present embodiment being executed by the processor, or the like, at the computer, it is possible to provide effects provided by the above-described processing relating to the information processing method according to the present embodiment being performed.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, the above shows that a program (computer program) causing a computer to function as the information processing apparatus according to the present embodiment is provided, but the present embodiment can further provide a recording medium caused to store the program.

The above configuration shows an example of the present embodiment and naturally comes under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art based on the description of this specification.

Additionally, the present technology may also be configured as below.

(1)

An information processing apparatus including:

a detection unit configured to detect a corneal reflection image corresponding to light from a light source reflected at a cornea from a captured image in which an eye irradiated with the light from the light source is imaged, wherein the detection unit estimates a position of a center of an eyeball on the basis of a plurality of time-series captured images each of which is the captured image according to the above, estimates a position of a center of the cornea on the basis of the estimated position of the center of the eyeball, estimates a position of a candidate for the corneal reflection image on the basis of the estimated position of the center of the cornea, and detects the corneal reflection image from the captured image on the basis of the estimated position of the candidate for the corneal reflection image.

(2)

The information processing apparatus according to (1), wherein the detection unit estimates, as the position of the center of the eyeball, a point of intersection of optical axis vectors at time points obtained on the basis of the plurality of captured images.

(3)

The information processing apparatus according to (1) or (2), wherein the detection unit estimates a position of a center of a pupil on the basis of the estimated position of the center of the eyeball, and estimates, as the position of the center of the cornea, a position that is on a line segment connecting the estimated position of the center of the eyeball and the estimated position of the center of the pupil and that is identified on the basis of information concerning the eye.

(4)

The information processing apparatus according to any one of (1) to (3), wherein the detection unit estimates the position of the candidate for the corneal reflection image on the basis of the estimated position of the center of the cornea, information concerning the eye, and a position of the light source.

(5)

The information processing apparatus according to any one of (1) to (4), wherein the detection unit detects an optical axis vector on the basis of a position of the detected corneal reflection image, information concerning the eye, and a position of the light source.

(6)

The information processing apparatus according to (5), wherein the detection unit detects the optical axis vector using two or more of the position of the center of the cornea identified on the basis of positions of a plurality of the detected corneal reflection images, information concerning the eye, and positions of light sources, a position of a center of a pupil identified on the basis of the identified position of the center of the cornea and information concerning the eye, and the estimated position of the center of the eyeball.

(7)

The information processing apparatus according to (5) or (6), wherein the detection unit corrects the optical axis vector using a set offset value.

(8)

The information processing apparatus according to any one of (5) to (7), further including a processing unit configured to perform processing using the optical axis vector.

(9)

The information processing apparatus according to (8), wherein the captured image is captured by an imaging device included in a device usable by being worn on a user's head or an external imaging device connected to the device usable by being worn on the user's head, and the processing unit detects a change in a wearing state of the device usable by being worn on the user's head on the basis of a distance between the optical axis vector detected at a first time point and the position of the center of the eyeball estimated at a second time point before the first time point.

(10)

The information processing apparatus according to any one of (1) to (9), further including an image recognition unit configured to recognize a pupil and the candidate for the corneal reflection image from the captured image, wherein the detection unit detects the corneal reflection image using a recognition result of the image recognition unit.

(11)

An information processing method executed by an information processing apparatus, the method including:

a step of detecting a corneal reflection image corresponding to light from a light source reflected at a cornea from a captured image in which an eye irradiated with the light from the light source is imaged, the step of detection including estimating a position of a center of an eyeball on the basis of a plurality of time-series captured images each of which is the captured image according to the above, estimating a position of a center of the cornea on the basis of the estimated position of the center of the eyeball, estimating a position of a candidate for the corneal reflection image on the basis of the estimated position of the center of the cornea, and detecting the corneal reflection image from the captured image on the basis of the estimated position of the candidate for the corneal reflection image.

(12)

A program for causing a computer to execute:

a step of detecting a corneal reflection image corresponding to light from a light source reflected at a cornea from a captured image in which an eye irradiated with the light from the light source is imaged, the step of detection including estimating a position of a center of an eyeball on the basis of a plurality of time-series captured images each of which is the captured image according to the above, estimating a position of a center of the cornea on the basis of the estimated position of the center of the eyeball, estimating a position of a candidate for the corneal reflection image on the basis of the estimated position of the center of the cornea, and detecting the corneal reflection image from the captured image on the basis of the estimated position of the candidate for the corneal reflection image.

REFERENCE SIGNS LIST

100 information processing apparatus
102 imaging unit
104 controller
110 image recognition unit
112 detection unit
114 processing unit

The invention claimed is:

1. An information processing apparatus comprising:
a detection unit configured to detect a corneal reflection image corresponding to light from a light source reflected at a cornea from a captured image in which an eye irradiated with the light from the light source is imaged,
wherein the captured image of the eye includes a pupil of the eye, an eyeball of the eye, and the cornea of the eye, wherein the detection unit
estimates a position of a center of the eyeball from the captured image on the basis of a plurality of time-series captured images each of which is the captured image according to the above,
estimates a position of a center of the pupil from the captured image on the basis of the estimated position of the center of the eyeball,
estimates a position of a center of the cornea from the captured image on the basis of the estimated position of the center of the eyeball and the estimated position of the center of the pupil,
estimates a position of a candidate for the corneal reflection image from the captured image on the basis of the estimated position of the center of the cornea, and
detects the corneal reflection image from the captured image on the basis of the estimated position of the candidate for the corneal reflection image,
wherein the position of the center of the pupil, the position of the center of the cornea, and the position of the center of the eyeball are different from each other, and
wherein the detection unit is implemented via at least one processor.

2. The information processing apparatus according to claim 1,
wherein the detection unit estimates, as the position of the center of the eyeball, a point of intersection of optical axis vectors at time points obtained on the basis of the plurality of time-series captured images.

3. The information processing apparatus according to claim 1,
wherein the detection unit
estimates, as the position of the center of the cornea, a position that is on a line segment connecting the estimated position of the center of the eyeball and the estimated position of the center of the pupil and that is identified on the basis of information concerning the eye.

4. The information processing apparatus according to claim 1,
wherein the detection unit estimates the position of the candidate for the corneal reflection image on the basis of the estimated position of the center of the cornea, information concerning the eye, and a position of the light source.

5. The information processing apparatus according to claim 1,
wherein the detection unit detects an optical axis vector on the basis of a position of the detected corneal reflection image, information concerning the eye, and a position of the light source.

6. The information processing apparatus according to claim 5,
wherein the detection unit detects the optical axis vector using two or more of
the position of the center of the cornea identified on the basis of positions of a plurality of the detected corneal reflection images, information concerning the eye, and positions of light sources,
a position of a center of a pupil identified on the basis of the identified position of the center of the cornea and information concerning the eye, and
the estimated position of the center of the eyeball.

7. The information processing apparatus according to claim 5,
wherein the detection unit corrects the optical axis vector using a set offset value.

8. The information processing apparatus according to claim 5, further comprising:
a processing unit configured to perform processing using the optical axis vector,
wherein the processing unit is implemented via at least one processor.

9. The information processing apparatus according to claim 8,
wherein the captured image is captured by an imaging device included in a device usable by being worn on a user's head or an external imaging device connected to the device usable by being worn on the user's head, and
the processing unit detects a change in a wearing state of the device usable by being worn on the user's head on the basis of a distance between the optical axis vector detected at a first time point and the position of the center of the eyeball estimated at a second time point before the first time point.

10. The information processing apparatus according to claim 1, further comprising:
an image recognition unit configured to recognize a pupil and the candidate for the corneal reflection image from the captured image,
wherein the detection unit detects the corneal reflection image using a recognition result of the image recognition unit, and
wherein the image recognition unit is implemented via at least one processor.

11. An information processing method executed by an information processing apparatus, the method comprising:
detecting a corneal reflection image corresponding to light from a light source reflected at a cornea from a captured image in which an eye irradiated with the light from the light source is imaged,
wherein the captured image of the eye includes a pupil of the eye, an eyeball of the eye and the cornea of the eye,
wherein the detection includes
estimating a position of a center of the eyeball from the captured image on the basis of a plurality of time-series captured images each of which is the captured image according to the above,
estimating a position of a center of the pupil from the captured image on the basis of the estimated position of the center of the eyeball,
estimating a position of a center of the cornea from the captured image on the basis of the estimated position of the center of the eyeball and the estimated position of the center of the pupil,
estimating a position of a candidate for the corneal reflection image from the captured image on the basis of the estimated position of the center of the cornea, and
detecting the corneal reflection image from the captured image on the basis of the estimated position of the candidate for the corneal reflection image, and
wherein the position of the center of the pupil, the position of the center of the cornea and the position of the center of the eyeball are different from each other.

12. A non-transitory computer-readable medium having embodied thereon a program, which when executed by a computer causes the computer to execute a method, the method comprising:

detecting a corneal reflection image corresponding to light from a light source reflected at a cornea from a captured image in which an eye irradiated with the light from the light source is imaged,
wherein the captured image of the eye includes a pupil of the eye, an eyeball of the eye and the cornea of the eye,
wherein the detection includes
- estimating a position of a center of the eyeball from the captured image on the basis of a plurality of time-series captured images each of which is the captured image according to the above,
- estimating a position of a center of the pupil from the captured image on the basis of the estimated position of the center of the eyeball,
- estimating a position of a center of the cornea from the captured image on the basis of the estimated position of the center of the eyeball and the estimated position of the center of the pupil,
- estimating a position of a candidate for the corneal reflection image from the captured image on the basis of the estimated position of the center of the cornea, and
- detecting the corneal reflection image from the captured image on the basis of the estimated position of the candidate for the corneal reflection image, and wherein the position of the center of the pupil, the position of the center of the cornea and the position of the center of the eyeball are different from each other.

* * * * *